United States Patent
Granier et al.

(10) Patent No.: US 10,494,323 B2
(45) Date of Patent: Dec. 3, 2019

(54) PROCESS FOR THE PREPARATION OF INDANONES

(71) Applicant: GIVAUDAN SA, Vernier (CH)

(72) Inventors: Thierry Granier, Duebendorf (CH); Yue Zou, Shanghai (CN)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/320,376

(22) PCT Filed: Aug. 14, 2017

(86) PCT No.: PCT/EP2017/070595
§ 371 (c)(1),
(2) Date: Jan. 24, 2019

(87) PCT Pub. No.: WO2017/191332
PCT Pub. Date: Nov. 9, 2017

(65) Prior Publication Data
US 2019/0263743 A1    Aug. 29, 2019

(30) Foreign Application Priority Data

Aug. 15, 2016    (WO) ................ PCT/CN2016/095275

(51) Int. Cl.
| | |
|---|---|
| C07C 45/00 | (2006.01) |
| C07C 269/00 | (2006.01) |
| C07B 37/00 | (2006.01) |
| C07C 45/51 | (2006.01) |
| C07C 49/697 | (2006.01) |
| C07B 37/10 | (2006.01) |
| C07C 311/07 | (2006.01) |
| C07C 269/06 | (2006.01) |

(52) U.S. Cl.
CPC ............ C07C 45/516 (2013.01); C07B 37/10 (2013.01); C07C 49/697 (2013.01); C07C 269/06 (2013.01); C07C 311/07 (2013.01); C07C 2602/08 (2017.05)

(58) Field of Classification Search
CPC ...... C07C 45/516; C07C 269/06; C07B 37/10
See application file for complete search history.

(56) References Cited

U.S. PATENT DOCUMENTS

| 3,944,679 A | 3/1976 | Takahara et al. |
| 7,250,528 B2 | 7/2007 | Womack et al. |

FOREIGN PATENT DOCUMENTS

| WO | 03072533 A1 | 9/2003 |
| WO | 2005100297 A1 | 10/2005 |

OTHER PUBLICATIONS

International Search Report and Written Opinion of the International Searching Authority for corresponding application PCT/EP2017/070595 dated Dec. 4, 2017.
Kraft, W.M.: "The Preparation of Indanone Derivatives by Carbamate-Aldehyde 1 Reaction", J. Am. Chem., vol. 70, No. 11, pp. 3569-3571.
Katritzky, A., et al: "Convenient Preparation of 1-Amidoindenes"; J. Org. Chem, Oct. 21, 2000, No. 23, vol. 65, pp. 8066-8068.
Womack, G., et al.: "Idanones and Idenols from 2-Alkylcinnamaldehydes via the Intramolecular Fridel-Crafts reaction of Germinal Diacetates"; J. Org. Chem, Jul. 2009, No. 15, vol. 74, pp. 5738-5741.
Womack, G., et al.:"Conversion of 2-Alkylcinnamaldehydes to 2-Alkylindanones via a Catalytic Intramolecular Fridel-Crafts reaction", J. Org. Chem, Aug. 2007, No. 18, vol. 72, pp. 7046-7049.
Xiaohui, F. et al.: "Assembly of indenamine derivatives through in situ formed N-sulfonyliminium ion initiated cylization", Chem Comm, vol. 50, No. 31, Jan. 1, 2014, pp. 4119-4122.
Chen, L., et al.: "Facile Syntheis of indene and fluorene derivatives through A1C1 3-catalyzed cyclization of in situ formed iminium ions", Applied Organometallic Chem., May 16, 2017, pp. 1-7.

Primary Examiner — Sikarl A Witherspoon
(74) Attorney, Agent, or Firm — Norris McLaughlin, PA

(57) ABSTRACT

A process of forming compounds of formula I

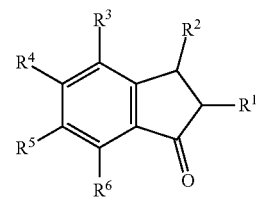

(I)

comprising the steps of addition of an amino compound $H_2NR$ to a compound of formula (II)

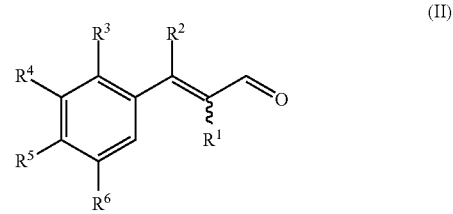

(II)

followed by cyclization, isomerization and hydrolysis.

4 Claims, No Drawings

PROCESS FOR THE PREPARATION OF INDANONES

This is an application filed under 35 USC 371 based on PCT/EP2017/070595, having an international filing date of 14 Aug. 2017, which in turn is based on PCT/CN2016/095275, filed 15 Aug. 2016. The present application claims the full priority benefit of these prior applications and herein incorporates by reference the full disclosures of these prior applications.

The present invention relates to the field of organic synthesis. It provides a novel process of preparing indanones, which are compounds of formula I:

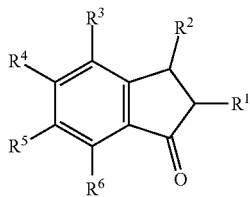

In particular, it provides a process of preparing compounds of formula I from α-substituted cinnamic aldehydes.

Some indanones have been described in literature as useful fragrance ingredients. For example, WO03072533 A1 describes the use of 3,3-dimethyl indanones in perfumery with leathery, woody and saffron-like odours. U.S. Pat. No. 3,944,679 disclosed 2- and 3-alkyl substituted indanones have coumarin-like odors when imparted to tobacco, foods and drinks flavors.

Often the synthetic pathway of indanones is somewhat complicated and the preparation has to be performed in several individual steps, adding to the costs of said compounds.

The synthesis of indenol esters and indenol ethers from cinnamic aldehydes has been disclosed in U.S. Pat. No. 7,250,528 B2. Said compounds can be further converted to the corresponding indanones (Womack, G. B. et al; J. Org. Chem. 2009, 74, 5738-5741; Womack, G. B. et al; J. Org. Chem. 2007, 72, 7046-7049).

Alternatively, indanones can be obtained from cinnamic aldehydes in a stepwise conversion via indenyl sulfonamides (Fan, X. et al; Chem. Comm. 2014, 50, 4119-4122) or indenyl carbamates (Kraft, W. M.; J. Am. Chem. Soc. 1948, 70, 3569-3571).

There remains a need to provide a simple and cost efficient process of producing compounds of formula I.

The invention provides in a first aspect a process of making a compound of formula (I)

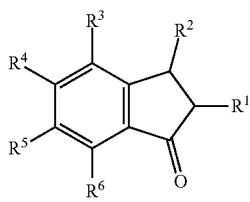

comprising the steps of:

a) condensation of an amino compound $H_2NR$ with a compound of formula (II)

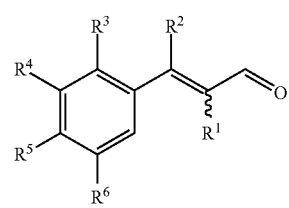

followed by cyclization to a compound of formula (III);

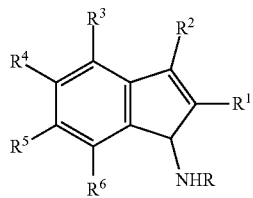

wherein the wavy bond in the compound of formula (II) indicates an unspecified configuration of the adjacent double bond; and the amino compound $H_2NR$ is selected from the group consisting of sulfonamides, carbamates and alkylamides;

b) isomerization of compound of formula (III) to a compound of formula (IV);

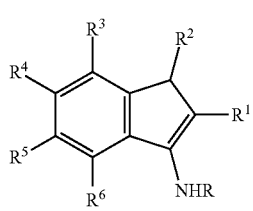

c) hydrolysis of compound of formula (IV) to compound of formula (I);

wherein, in the compounds of formula (I), (II), (III) and/or (IV), $R^1$ represents methyl, ethyl, ethenyl, a linear, branched or cyclic $C_{3-10}$ alkyl or alkenyl group, or a phenyl group, optionally substituted;

$R^2$, $R^3$, $R^4$, $R^5$ and $R^6$ each independently represent a hydrogen atom, methyl, ethyl, ethenyl, methoxy, ethoxy, ethenoxy, a linear, branched or cyclic $C_{3-10}$ alkyl, alkenyl or alkoxy group, a halogen atom or a phenyl group, optionally substituted.

In general, such an optionally substituted phenyl group might bear one or more substituents selected from the group consisting of a linear, branched or cyclic alkyl, alkenyl or alkoxy group or a halogen atom, for example.

In step a) of the process, an α-substituted cinnamic aldehyde of formula (II) undergoes a condensation reaction with an amino compound $H_2NR$, followed by immediate cyclization to an indenyl amine intermediate compound of formula (III):

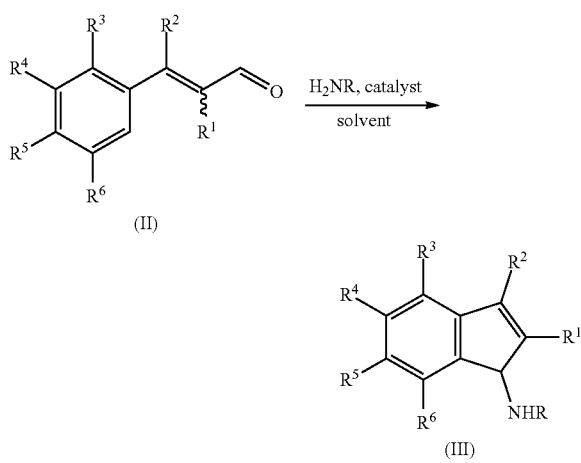

The wavy bond in the compound of formula (II) indicates an unspecified configuration of the adjacent double bond. It means that the compound of formula (II) can be present as E- or Z-compound, or as an isomeric mixture.

The amino compound $H_2NR$ is selected from sulfonamides, carbamates or alkylamides.

In an embodiment where amino compound $H_2NR$ is selected from sulfonamides, then R represents in particular $-SO_2Me$, $-SO_2Et$ or $-SO_2PhMe$.

Amongst the above mentioned amino compounds $H_2NR$, the sulfonamides are the most expensive; however, when employed in step a) of the process, the reaction proceeds fast.

In an embodiment where amino compound $H_2NR$ is selected from carbamates, then R represents in particular $-CO_2Me$ or $-CO_2Et$.

When carbamates are selected as amino compound $H_2NR$ the reaction might lead to very few or almost no by-products.

In an embodiment where amino compound $H_2NR$ is selected from alkylamides, then R represents in particular $-(CO)Me$ or $-(CO)Et$.

Alkylamides are the cheapest alternatives amongst the mentioned amino compounds $H_2NR$, but the reaction according to step a) of the process is slower. However, the reaction is giving good yields. This is surprising in knowledge of prior art (Fan, X. et al; Chem. Comm. 2014, 50, 4119-4122), where the analogue reaction using benzamide (R=—(CO)Ph) failed to give the desired product.

The amino compound $H_2NR$ can be employed in 1.0 to 1.2, preferably in 1.05 to 1.1 molar equivalents, relative to the molar amount of compound of formula (II). The optimum concentration of the amino compound depends on its nature and on further reaction conditions.

The condensation reaction of step a) is catalysed for example by a Lewis acid, which might be selected from (but is not limited to) the group consisting of $FeCl_3$, $ZnCl_2$, $AlCl_3$, $TiCl_4$, $BF_3$, $ZnBr_2$, or another activating agent, for an example $POCl_3$, $PCl_5$ or TfOH. Said compounds can be in the anhydrous form (for example $FeCl_3$) or also in the hydrate form (for example $FeCl_3.6H_2O$), except for those acids which are unstable in the presence of water.

The Lewis acid can be employed in catalytic or stoichiometric amounts or even in excess. Preferably, the catalyst is employed in 0.01 to 0.5, or even between 0.1-0.2 molar equivalents, relative to the molar amount of compound of formula (II). However, the optimum concentration of catalyst depends on the nature of the catalyst and on further reaction conditions.

In one aspect of the invention, the catalyst for the condensation reaction of step a) is a Lewis acid, in particular $FeCl_3$.

In one aspect of the invention, step a) is carried out preferably in a solvent selected from the group consisting of toluene, xylene, benzene, dichloromethane 1,2-dichloroethane, EtOAc, MeOAc or acetonitrile.

The required amount of the solvent depends on the solubility of the reaction partners, and in particular on the solubility of compound of formula (II). For economic reasons, the amount of the solvent is preferably low, for example in the ratio 1:10, or 1:7, or 1:4, or 1:3, or even 1:1.5 of starting aldehyde (g) to solvent (ml).

Step a) of the process can be carried out at room temperature. Alternatively, the reaction mixture can be heated up to 65 or 75° C., or to reflux, and the optimal temperature depends on the selected solvent and/or the employed catalyst. In general, an elevated temperature might shorten the reaction time.

Depending on the substituents $R^3$ to $R^6$ at the aromatic ring in the compound of formula (II), the cyclization step might lead to one compound of formula (III) or to a mixture of two isomers. For example, two isomers can be obtained if there is only a substituent at position 3 of the phenyl ring, for example $R^4$=Me and $R^3$, $R^5$ and $R^6$=H in the compound of formula (II). Both isomers can be converted further in the subsequent steps.

In step b) of the process, an isomerization of indenyl amine intermediate compound of formula (III) to an intermediate compound of formula (IV) takes place:

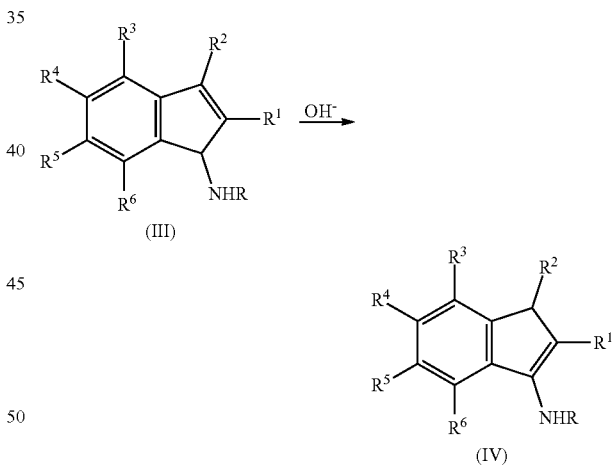

The isomerization is performed in the presence of a base, for example a diluted aqueous base or in alcoholic solution, in different concentrations, for example 1 molar, 2 molar or 32%. Preferably the base is an alkali base, for example NaOH. Alternatively, $Et_3N$ or other amines such DABCO in an organic solvent such as EtOAc can be used.

The base can be employed in 0.5 to 2.5, preferably in 0.89 to 1.7, more preferably in 1.5 molar equivalents, relative to the molar amount of compound of formula (II). With a higher amount of the base the reaction time might be shortened.

In step c) of the process, intermediate compound of formula (IV) is hydrolysed to the desired indanon compound of formula I:

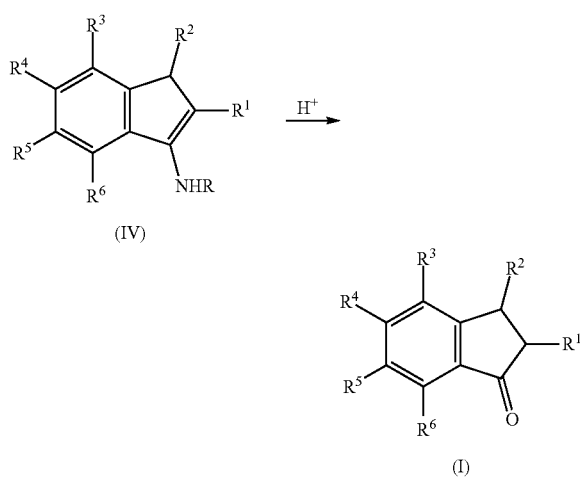

(IV)

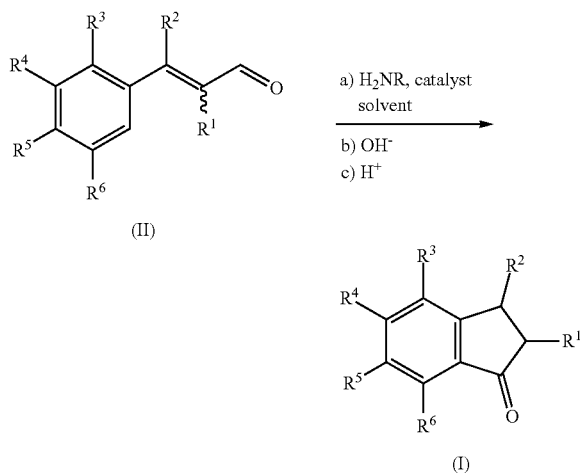

The hydrolysis is preferably performed by treatment with a Bronsted acid. It might be accelerated at elevated temperature.

Preferably, the employed Bronsted acid is $H_2SO_4$ or HCl, and it is used in concentrated or in diluted form.

The Bronsted acid can be employed in 1.0 to 3.0, preferably in 1.1 to 2.7, more preferably in 1.7 molar equivalents, relative to the molar amount of compound of formula (II).

In a particular embodiment, the steps a), b) and c) of the process are carried out in a one-pot procedure wherein, in the compounds of formula (I) and/or (II), $R^1$ represents methyl, ethyl, ethenyl, a linear, branched or cyclic $C_{3-10}$ alkyl or alkenyl group, or a phenyl group, optionally substituted;

$R^2$, $R^3$, $R^4$, $R^5$ and $R^6$ each independently represent a hydrogen atom, methyl, ethyl, ethenyl, methoxy, ethoxy, ethenoxy, a linear, branched or cyclic $C_{3-10}$ alkyl, alkenyl or alkoxy group, a halogen or a phenyl group, optionally substituted.

Such a one-pot procedure allows for a faster synthesis of indanones, because only one work-up and/or purification step of the final compound of formula (I) is required instead of three. Thereby, also the consumption of solvents can be reduced, making the process environmentally friendly and further reducing costs.

In addition, the one-pot procedure might give higher yield than the overall yield of the stepwise process.

Furthermore, as the indenyl amine intermediates—the compounds of formula (III) and (IV)—are solids while the final product is an oil, avoiding the isolation of these intermediates using the three step-one pot procedure, might be more convenient.

In an aspect of the invention, the process described above is useful to obtain compounds of formula (I) with a molecular weight of not more than 300 g/mol. Such compounds are particularly useful fragrances.

In one aspect of the invention, the process described above is useful to obtain a compound of formula (I), wherein in the compounds of formula (I), (II), (III) and/or (IV), $R^1$ is selected from the group consisting of methyl, ethyl, propyl and iso-propyl.

In a further aspect of the invention, the process described above is useful to obtain a compound of formula (I), wherein in the compounds of formula (I), (II), (III) and/or (IV), $R^2$ is selected from the group consisting of H and methyl.

In a further aspect of the invention, the process described above is useful to obtain a compound of formula (I), wherein in the compounds of formula (I), (II), (III) and/or (IV), $R^3$, $R^4$, $R^5$ and $R^6$ are independently selected from the group consisting of H, methyl, ethyl, propyl, iso-propyl, cyclo-propyl, butyl, iso-butyl, sec-butyl, tert-butyl, cyclo-butyl, pentyl, iso-pentyl, cyclo-pentyl, methoxy, ethoxy, propoxy, iso-propoxy, butoxy, iso-butoxy, Cl, Br, I and phenyl, optionally substituted.

In particular, said process is useful to react an amino compound with the compound of formula (II) having electron withdrawing groups on the phenyl ring, for example a halogen atom like Cl, Br, I, and then further convert it to the corresponding indanone. This is surprising, as the addition reaction failed under the conditions described by Fan, X. et al (Chem. Comm. 2014, 50, 4119-4122).

In a further aspect of the invention, the process described above is useful to obtain a compound of formula (I), wherein in the compounds of formula (I), (II), (III) and/or (IV), at least one of $R^3$, $R^4$, $R^5$ and $R^6$ is a H, while the other substituents of that group are independently selected from the group consisting of methyl, ethyl, ethenyl, methoxy, ethoxy, ethenoxy, a linear, branched or cyclic $C_{3-10}$ alkyl, alkenyl or alkoxy group, a halogen or a phenyl group, optionally substituted.

In a further aspect of the invention, the process described above is useful to obtain a compound of formula (I), wherein in the compounds of formula (I), (II), (III) and/or (IV), at least two or three of $R^3$, $R^4$, $R^5$ and $R^6$ are representing a H, while the other substituent(s) of that group is/are independently selected from the group consisting of methyl, ethyl, ethenyl, methoxy, ethoxy, ethenoxy, a linear, branched or cyclic $C_{3-10}$ alkyl, alkenyl or alkoxy group, a halogen or a phenyl group, optionally substituted.

In a particular embodiment of the invention, the process described above is useful to obtain a compound of formula (I), wherein in the compounds of formula (I), (II), (III) and/or (IV), $R^1$ is selected from the group consisting of methyl, ethyl, propyl and iso-propyl;

$R^2$ is selected from the group consisting of H and methyl; and $R^3$, $R^4$, $R^5$ and $R^6$ are independently selected from the group consisting of H, methyl, ethyl, propyl, iso-propyl, cyclo-propyl, butyl, iso-butyl, sec-butyl, tert-butyl, cyclo-butyl, pentyl, iso-pentyl, cyclo-pentyl, methoxy, ethoxy, propoxy, iso-propoxy, butoxy, iso-butoxy, Cl, Br, I and phenyl, optionally substituted.

In a further aspect of the invention, the process described above is useful to obtain a compound of formula (I), wherein in the compound of formula (II), $R^3$, $R^5$ and $R^6$ are representing H, and $R^4$ is selected from the group consisting of H, methyl, ethyl, propyl, iso-propyl, cyclo-propyl, butyl, iso-butyl, sec-butyl, tert-butyl, cyclo-butyl, pentyl, iso-pentyl, cyclo-pentyl, methoxy, ethoxy, propoxy, iso-propoxy, butoxy, iso-butoxy, Cl, Br, I and phenyl, optionally substituted. In this case, the process described above will give mixture of regioisomeric compounds of formula (I).

In a further aspect of the invention, the process described above is useful to obtain a compound of formula (I) selected from 6-Isobutyl-2-methyl-2,3-dihydro-1H-inden-1-one and 2-Isopropyl-6-methyl-2,3-dihydro-1H-inden-1-one.

The invention is now further described with reference to the following non-limiting examples. These examples are for the purpose of illustration only and it is understood that variations and modifications can be made by one skilled in the art.

EXAMPLES

Example 1: Preparation of 6-Isobutyl-2-methyl-2,3-dihydro-1H-inden-1-one—Stepwise Synthesis Using Methyl Carbamate (MeOCONH$_2$)

Step 1: Methyl (6-isobutyl-2-methyl-1H-inden-1-yl)carbamate

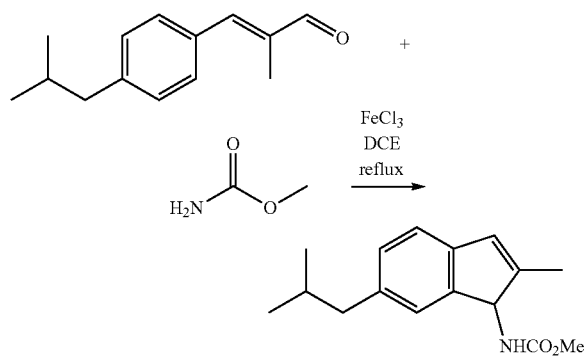

A mixture of methyl carbamate (39.4 g, 0.519 mol, 1.05 eq.) and (E)-3-(4-isobutylphenyl)-2-methylacrylaldehyde (dehydrosilvial, 100 g, 0.494 mol, 1-2% (Z)-isomer) in dichloroethane (400 ml) was heated to 35° C. and the resulting solution was treated with iron trichloride (8.27 g, 0.049 mol, 0.1 eq.). The resulting mixture was heated to reflux (79° C.), stirred for 2 h, cooled to 15° C., treated with EtOAc (100 ml), and washed with 1N aq. HCl (80 ml). The organic phase was washed twice with aqueous saturated NaHCO$_3$ (50 ml), twice with aqueous saturated NaCl (50 ml), dried with MgSO$_4$, filtered, and the solvent evaporated. The crude product (120 g, brown solid) was triturated with hexane (300 ml), filtered, washed with hexane (150 ml), and dried, giving methyl (6-isobutyl-2-methyl-1H-inden-1-yl)carbamate (91 g, 92% pure, slightly brown-coloured solid, 71% yield).

R$_f$ (hexane/MTBE 10:1): 0.25; $^1$H-NMR (400 MHz, CDCl$_3$): δ 7.19 (br. s, 1H), 7.05 (br. d, J=7.6, 1H), 7.01 (br. d, J=7.3, 1H), 6.35 (br. s, 1H), 5.20 (br. d, J=9.8, 1H), 4.65 (br. d, J=9.5, 1H), 3.78 (br. s, OMe), 2.46 (d, J=7.1, CH$_2$), 2.02 (s, Me), 1.85 (hept., J=6.7, 1H), 0.91 (d, J=6.6, CMe$_2$); $^{13}$C-NMR (100 MHz, CDCl$_3$): δ 157.78 (s), 145.72 (s), 144.22 (s), 141.08 (s), 138.60 (s), 128.84 (d), 127.47 (d), 124.15 (d), 119.62 (d), 60.41 (d), 52.44 (q), 45.34 (t), 30.38 (d), 22.35 (2q), 13.96 (q); MS (EI): 260 (10), 259 (53), 244 (5), 227 (10), 216 (47), 202 (29), 185 (21), 184 (100), 170 (14), 156 (42), 142 (43), 141 (96), 128 (26), 115 (32).

Step 2: Methyl (5-isobutyl-2-methyl-1H-inden-3-yl)carbamate

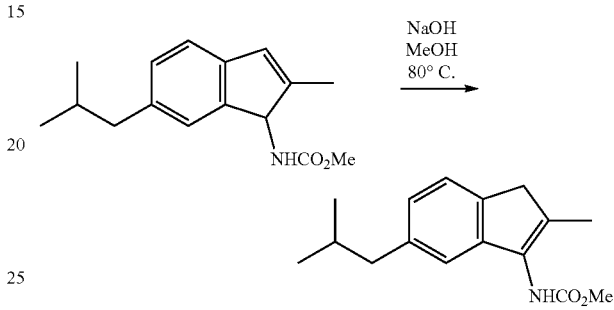

At 50° C., a solution of methyl (6-isobutyl-2-methyl-1H-inden-1-yl)carbamate (90 g, 0.347 mol) in MeOH (230 ml) was treated dropwise with 2M aq. NaOH (87 ml, 0.174 mol, 0.5 eq.) while the reaction temperature was increased to reflux temperature to allow stirring. The resulting mixture was stirred at reflux for 2 h, cooled, treated with ice (100 g), and extracted with MTBE (1 l). The organic phase was washed with aq. sat. NH$_4$Cl soln. (100 ml), twice with aq. sat. NaCl soln. (100 ml), dried over MgSO$_4$, filtered, and the solvent evaporated. The crude product (85.5 g, brown solid) was triturated with hexane (300 ml), filtered, washed with hexane (150 ml), and dried, giving methyl (5-isobutyl-2-methyl-1H-inden-3-yl)carbamate (74.5 g, 89% pure, slightly brown-coloured solid, 74% yield).

R$_f$ (hexane/MTBE 10:1): 0.13; $^1$H-NMR (400 MHz, CDCl$_3$): δ 7.23 (br. d, J=7.3, 1H), 6.96 (br. s, 1H), 6.92 (br. dd, J=1.4, 7.5, 1H), 6.13 (br. s, 1H), 3.76 (br. s, OMe), 3.27 (br. s, CH$_2$), 2.49 (d, J=7.1, CH$_2$), 2.04 (s, Me), 1.86 (hept., J=6.7, 1H), 0.90 (d, J=6.6, CMe$_2$); $^{13}$C-NMR (100 MHz, CDCl$_3$): δ 157.07 (br. s), 142.57 (s), 139.73 (s), 138.22 (s), 135.65 (br. s), 131.00 (br. s), 125.38 (d), 122.99 (d), 118.20 (br. d), 52.54 (q), 45.53 (t), 40.27 (t), 30.42 (d), 22.37 (2q), 13.77 (br. q).

MS (EI): 260 (6), 259 (34), 244 (4), 227 (25), 216 (29), 202 (18), 185 (17), 184 (100), 170 (23), 156 (29), 142 (28), 141 (56), 128 (20), 115 (22).

Step 3: 6-Isobutyl-2-methyl-2,3-dihydro-1H-inden-1-one

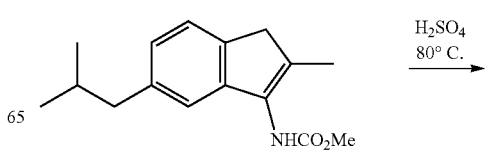

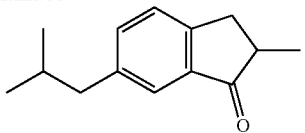

A suspension of methyl (5-isobutyl-2-methyl-1H-inden-3-yl)carbamate (73 g, 0.28 mol) in methanol (70 ml) and 35% aq. sulfuric acid (87 g, 0.31 mol, 1.1 eq.) was heated at reflux (80° C.) for 1 h, cooled, and extracted with MTBE (100 ml). The org. phase was washed with 2M aq. HCl and the combined aq. phases were extracted twice with MTBE (70 ml). The combined org. phases were washed with aqueous saturated NaHCO$_3$ (100 ml), with aqueous saturated NaCl (100 ml), filtrated, and the filtrate dried with MgSO$_4$, filtered, and the solvent evaporated. The crude product (53 g) was distilled using a short-path Vigreux-distillation apparatus (0.1 mbar, oil bath temperature: 155 to 175° C., head temperature 98-115° C.) giving 6-isobutyl-2-methyl-2,3-dihydro-1H-inden-1-one (49.5 g, 99.6% pure, yellow oil, 87% yield).

R$_f$ (hexane/MTBE 10:1): 0.48; $^1$H-NMR (400 MHz, CDCl$_3$): δ 7.53 (br. s, 1H), 7.38 (dd, J=1.5, 7.8, 1H), 7.34 (br. dm, J=0.7, 7.8, 1H), 3.35 (m, 1H), 2.75-2.64 (m, 2H), 2.52 (d, J=7.1, CH$_2$), 1.87 (hept., J=6.7, 1H), 1.30 (d, J=7.6, Me), 0.90 (d, J=6.6, CMe$_2$); $^{13}$C-NMR (100 MHz, CDCl$_3$): δ 209.5 (s), 151.0 (s), 141.0 (s), 136.3 (s), 135.9 (d), 126.0 (d), 123.9 (d), 44.8 (t), 42.2 (d), 34.5 (t), 30.1 (d), 22.2 (2q), 16.2 (q); MS (EI): 203 (5), 202 (34), 187 (8), 160 (71), 159 (100), 145 (26), 141 (6), 131 (14), 129 (11), 128 (14), 116 (12), 115 (27), 91 (13), 77 (6).

Yield over 3 steps: 46%

Example 2a: Preparation of 6-Isobutyl-2-methyl-2,3-dihydro-1H-inden-1-one—One-Pot Synthesis Using Methyl Carbamate (MeOCONH$_2$)

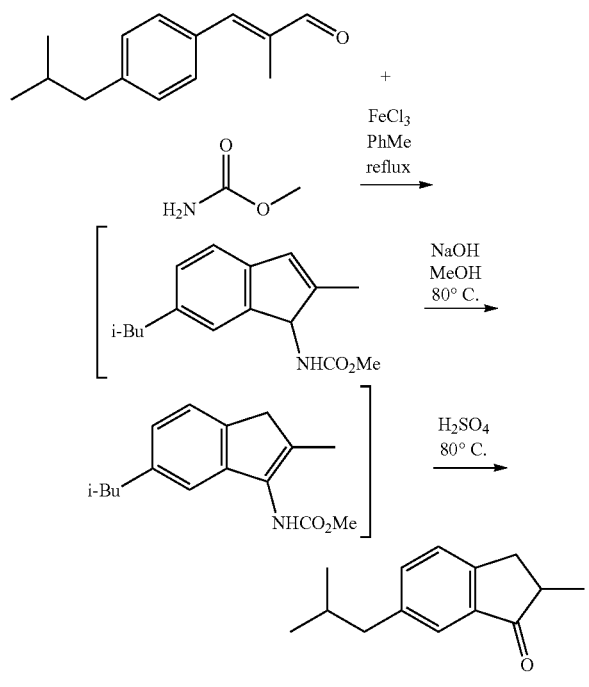

A mixture of (E)-3-(4-isobutylphenyl)-2-methylacrylaldehyde (dehydrosilvial, 5 g, 24.7 mmol, 1-2% (Z)-isomer) and methyl carbamate (2 g, 26 mmol, 1.05 eq.) in toluene (20 ml) was treated with iron trichloride (0.4 g, 2.47 mmol, 0.1 eq.), and heated at reflux temperature for 30 min. The reaction mixture was then cooled to 45° C., treated with 2N aq. NaOH (11 ml) and methanol (5 ml) and stirred at reflux temperature for 21 h. The resulting mixture was cooled to 55° C., treated with conc. H$_2$SO$_4$ (1.85 g), stirred at reflux temperature for 10 h, and cooled to 20° C. The aq. phase was separated and the org. phase was diluted with MTBE (25 ml) and washed with 2N aq. HCl. The combined aq. phases were extracted twice with MTBE (10 ml) and the combined organic phases were washed with aq. sat. NaHCO$_3$ (10 ml), twice with aq. sat. NaCl (10 ml), dried with MgSO$_4$, filtered, and the solvent evaporated. The crude product (5.6 g, brown oil) was distilled using a Kugelrohr apparatus (150-200° C., 0.08-0.1 mbar) giving 6-isobutyl-2-methyl-2,3-dihydro-1H-inden-1-one as characterized in Example 1 (3.97 g, 93% pure, yellow oil, 74% yield).

Example 2b: Alternatively, the Following Conditions can be Applied

A mixture of (E)-3-(4-isobutylphenyl)-2-methylacrylaldehyde (dehydrosilvial, 20 g, 99 mmol, 1-2% (Z)-isomer), iron trichloride (2.455 g, 14.8 mmol, 0.15 eq.), and toluene (8 ml) was warmed to 73-75° C. and treated dropwise (25 min) with a warm solution (40° C.) of methyl carbamate (7.5 g, 99 mmol, 1.0 eq.) in toluene (22 ml). The resulting mixture was heated at 75° C. for 80 min, treated dropwise first with methanol (15 ml) and then with 32% aq. NaOH (18.54 g, 1.5 eq.) and stirred at reflux temperature (60° C.) for 30 min. The resulting mixture was treated with conc. H$_2$SO$_4$ (17.35 g, 1.7 eq.), stirred at reflux temperature (60° C.) for 30 min, cooled to 20° C., treated with hexane (40 ml) and 2M aq. HCl (60 ml). The aq. phase was separated and the org. phase was diluted with MTBE (25 ml) and washed with 2N aq. HCl. The combined aq. phases were extracted three times with hexane (25 ml) and the combined organic phases were washed with aq. sat. NaHCO$_3$ (50 ml), twice with aq. sat. NaCl (50 ml), dried with MgSO$_4$, filtered, and the solvent evaporated. The crude product (20.1 g, brown oil) was distilled using a short-path distillation apparatus (120-180° C., 0.08 mbar) giving 6-isobutyl-2-methyl-2,3-dihydro-1H-inden-1-one (16.2 g, 95% pure, yellow oil, 77% yield).

Example 3: Preparation of 6-Isobutyl-2-methyl-2,3-dihydro-1H-inden-1-one—One-Pot Synthesis Using Ethyl Carbamate (EtOCONH$_2$)

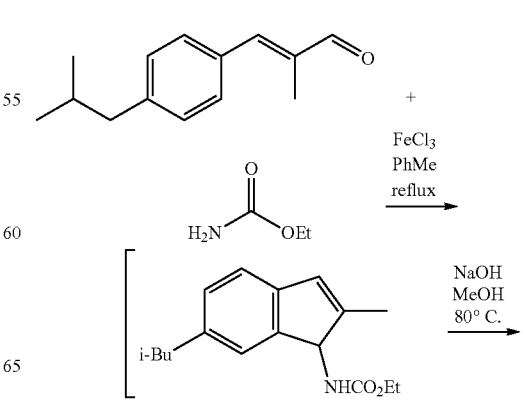

-continued

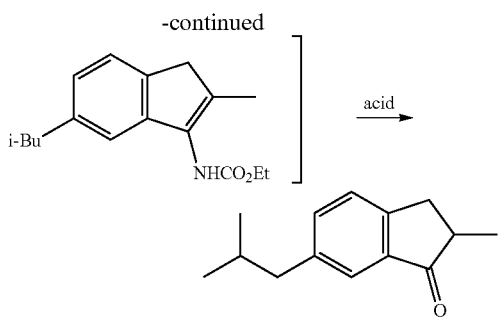

A mixture of (E)-3-(4-isobutylphenyl)-2-methylacrylaldehyde (dehydrosilvial, 3 g, 14.8 mmol, 1-2% (Z)-isomer) and ethyl carbamate (1.3 g, 14.8 mmol, 1 eq.) in toluene (30 ml) was treated with iron trichloride (360 mg, 2.2 mmol, 0.15 eq.), and heated at reflux temperature for 50 min. The reaction mixture was then cooled to 10° C., treated with 2N aq. NaOH (10 ml) and methanol (11 ml) and stirred at reflux temperature for 4 h. The resulting mixture was cooled to 15° C., treated with conc. HCl (2.5 ml), stirred at reflux temperature for 13 h, cooled, and poured into ice. The aq. phase was separated and extracted three times with MTBE. The combined organic phases were washed with aq. sat. NaHCO$_3$, twice with aq. sat. NaCl, dried with MgSO$_4$, filtered, and the solvent evaporated. The crude product (3.94 g, brown oil) was distilled using a Kugelrohr apparatus (170-190° C., 0.1 mbar) giving 6-isobutyl-2-methyl-2,3-dihydro-1H-inden-1-one as characterized in Example 1 (3 g, 84% pure, yellow oil, 84% yield).

Intermediate 1 (Ethyl (6-isobutyl-2-methyl-1H-inden-1-yl)carbamate)

$^1$H-NMR (400 MHz, CDCl$_3$): δ 7.18 (br. s, 1H), 7.02 (br. d, J=7.6, 1H), 6.97 (br. d, J=7.6, 1H), 6.33 (br. m, 1H), 5.18 (br. d, J=9.8, 1H), 4.69 (br. d, J=9.8, 1H), 4.20 (q, J=7.1, OCH$_2$), 2.44 (d, J=7.3, CH$_2$), 1.99 (s, Me), 1.83 (hept., J=6.7, 1H), 1.27 (d, J=7.1, Me). 0.89 (d, J=6.6, CMe$_2$); $^{13}$C-NMR (100 MHz, CDCl$_3$): δ 157.4 (s), 145.8 (s), 144.3 (s), 141.0 (s), 138.4 (s), 128.7 (d), 124.1 (d), 119.5 (br. d), 61.1 (t), 60.3 (d), 45.3 (t), 30.3 (d), 22.3 (2q), 14.5 (q), 13.9 (br. q); MS (EI): 274 (10), 273 (52), 258 (2), 244 (13), 230 (22), 227 (15), 216 (10), 200 (16), 185 (23), 184 (100), 170 (16), 156 (35), 142 (41), 141 (77), 128 (26), 115 (30).

Intermediate 2 (Ethyl (5-isobutyl-2-methyl-1H-inden-3-yl)carbamate)

$^1$H-NMR (400 MHz, CDCl$_3$): δ 7.25 (br. d, J=7.3, 1H), 6.99 (br. s, 1H), 6.94 (br. dd, J=1.3, 7.5, 1H), 6.22 (br. s, 1H), 4.23 (q, J=7.1, 14.2, OCH$_2$), 3.29 (br. s, CH$_2$), 2.51 (d, J=7.1, CH$_2$), 2.06 (s, Me), 1.88 (hept., J=6.7, 1H), 1.23 (t, J=7.0, Me). 0.92 (d, J=6.6, CMe$_2$); $^{13}$C-NMR (100 MHz, CDCl$_3$): δ 157.5 (br. s), 142.7 (s), 139.8 (s), 138.3 (s), 135.4 (br. s), 131.1 (br. s), 125.4 (d), 123.0 (d), 118.3 (br. d), 61.4 (br. t), 45.6 (t), 40.3 (t), 30.5 (d), 22.4 (2q), 14.6 (q), 13.9 (br. q); MS (EI): 274 (5), 273 (27), 244 (7), 230 (9), 227 (34), 216 (4), 200 (9), 185 (18), 184 (100), 170 (24), 156 (20), 142 (20), 141 (37), 128 (17), 115 (17).

Example 4: Preparation of 6-Isobutyl-2-methyl-2,3-dihydro-1H-inden-1-one—One-Pot Synthesis Using Methanesulfonamide (MeSO$_2$NH$_2$)

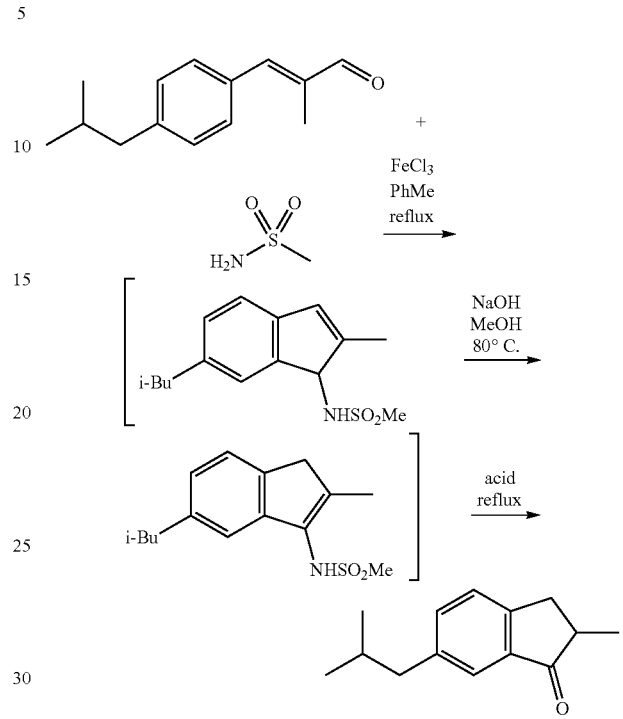

A mixture of (E)-3-(4-isobutylphenyl)-2-methylacrylaldehyde (dehydrosilvial, 50 g, 247 mmol, 1-2% (Z)-isomer) and methanesulfonamide (25.2 g, 260 mmol, 1.05 eq.) in toluene (300 ml) was treated with iron trichloride (4.13 g, 24.7 mmol, 0.1 eq.), and heated at reflux temperature (98° C.) for 4 h. The reaction mixture was then cooled to 25° C., treated with methanol (50 ml) and 2N aq. NaOH (144 ml) and stirred for 2.5 h. The resulting mixture was treated dropwise with conc. HCl (53 ml), stirred at reflux temperature for 24 h, cooled, and poured into ice. The aq. phase was separated and extracted three times with MTBE. The combined organic phases were washed with aq. sat. NaHCO$_3$, twice with aq. sat. NaCl, dried with MgSO$_4$, filtered, and the solvent evaporated. The crude product (57 g, brown oil) was distilled (oil bath temperature 120-130° C.) using a short-path Vigreux distillation apparatus (head temperature 100° C., 0.06 mbar) giving 6-isobutyl-2-methyl-2,3-dihydro-1H-inden-1-one as characterized in Example 1 (36.1 g, 85% pure, yellow oil, 61% yield).

Intermediate 1 (N-(6-Isobutyl-2-methyl-1H-inden-1-yl)methanesulfonamide)

$^1$H-NMR (400 MHz, CDCl$_3$): δ 7.24 (br. s, 1H), 7.01 (br. d, J=7.3, 1H), 6.98 (br. dd, J=1.2, 7.6, 1H), 6.34 (br. m, 1H), 4.73 (br. d, J=9.8, 1H), 4.50 (br. d, J=9.8, 1H), 3.10 (s, SO$_2$Me), 2.45 (d, J=7.1, CH$_2$), 2.05-2.04 (2d, J=1.0, Me), 1.84 (hept., J=6.7, 1H), 0.90 (d, J=6.6, Me), 0.89 (d, J=6.6, Me); $^{13}$C-NMR (100 MHz, CDCl$_3$): δ 144.4 (s), 143.6 (s), 140.6 (s), 138.9 (s), 129.2 (d), 127.9 (d), 124.3 (d), 119.9 (d), 62.5 (d), 45.3 (t), 42.4 (q), 30.3 (d), 22.3 (2q), 14.0 (q); MS (EI): 279 (20), 264 (1), 236 (2), 200 (89), 199 (17), 184 (7), 172 (9), 157 (33), 156 (100), 142 (24), 141 (24), 130 (18), 128 (21), 115 (20).

Intermediate 2 (N-(5-isobutyl-2-methyl-1H-inden-3-yl)methanesulfonamide)

$^1$H-NMR (400 MHz, CDCl$_3$): δ 7.25 (br. dm, J=7.8, 1H), 7.15 (br. s, 1H), 6.96 (br. dd, J=1.5, 7.6, 1H), 6.42 (br. s, 1H), 3.32 (br. s, CH$_2$), 2.99 (s, SO$_2$Me), 2.51 (d, J=7.1, CH$_2$), 2.18 (s, Me), 1.86 (hept., J=6.7, 1H), 0.90 (d, J=6.6, CMe$_2$); $^{13}$C-NMR (100 MHz, CDCl$_3$): δ 142.2 (s), 142.0 (s), 140.1 (s), 138.1 (s), 130.2 (s), 125.9 (d), 123.3 (d), 118.4 (d), 45.4 (t), 40.5 (q), 40.5 (t), 30.4 (d), 22.3 (2q), 14.0 (q); MS (EI): 279 (24), 264 (1), 237 (4), 236 (4), 200 (100), 172 (13), 158 (40), 156 (50), 142 (27), 130 (35), 116 (15), 115 (20).

Example 5: Preparation of 6-Isobutyl-2-methyl-2,3-dihydro-1H-inden-1-one—One-Pot Synthesis Using Acetamide (MeCONH$_2$)

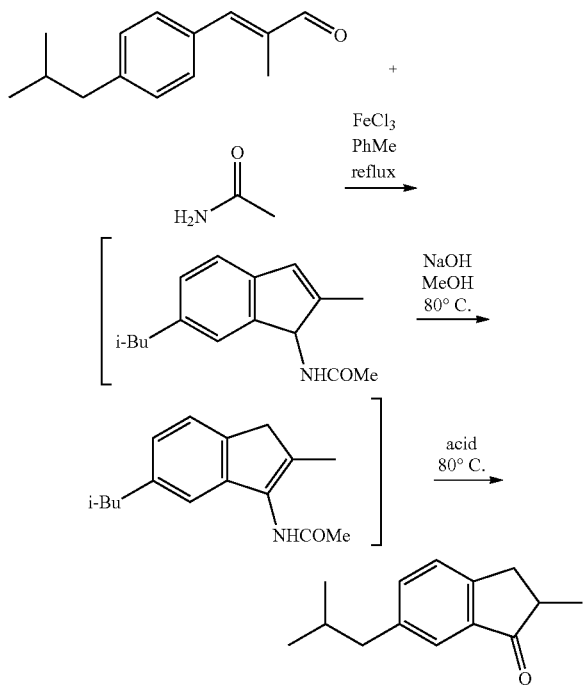

A mixture of (E)-3-(4-isobutylphenyl)-2-methylacrylaldehyde (dehydrosilvial, 1 g, 4.94 mmol, 1-2% (Z)-isomer) and acetamide (0.32 g, 5.42 mmol, 1.1 eq.) in toluene (10 ml) was treated with iron trichloride (180 mg, 1.1 mmol, 0.2 eq.), and heated at reflux temperature (104° C.) for 24 h. The reaction mixture was then cooled to 10° C., treated with 2N aq. NaOH (3 ml) and stirred at 20° C. for 2 h and at reflux temperature for 2.5 h. The resulting mixture was treated with conc. HCl (1 ml), stirred at reflux temperature for 15 h, cooled, and poured into ice. The aq. phase was separated and extracted twice with MTBE. The combined organic phases were washed with aq. sat. NaHCO$_3$, twice with aq. sat. NaCl, dried with MgSO$_4$, filtered, and the solvent evaporated. The crude product (1.1 g, brown oil) was distilled using a Kugelrohr apparatus (170-190° C., 0.1 mbar) giving 6-isobutyl-2-methyl-2,3-dihydro-1H-inden-1-one as characterized in Example 1 (0.93 g, 84% pure, yellow oil, 65% yield).

Example 6: Preparation of 6-Isobutyl-2-methyl-2,3-dihydro-1H-inden-1-one—Stepwise Synthesis Using Acetamide (MeCONH$_2$)

Step 1:
N-(6-isobutyl-2-methyl-1H-inden-1-yl)acetamide

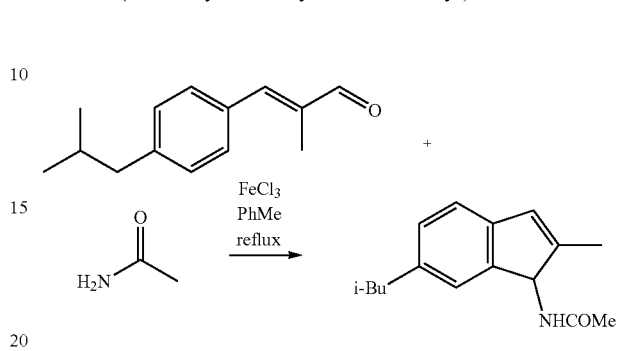

A mixture of acetamide (1.6 g, 27.1 mmol, 1.1 eq.) and (E)-3-(4-isobutylphenyl)-2-methylacrylaldehyde (dehydrosilvial, 5 g, 24.7 mmol, 1-2% (Z)-isomer) in toluene (50 ml) was heated to 50° C. and the resulting solution was treated with iron trichloride (0.80 g, 4.94 mmol, 0.2 eq.). The resulting mixture was heated to reflux (100° C.), stirred for 20 h, cooled to 60° C., treated with EtOAc (20 ml), and washed with 1N aq. HCl (10 ml). The organic phase was washed with aqueous saturated NaHCO$_3$ (10 ml), three times with aqueous saturated NaCl (10 ml) and the final organic phase (suspension) was filtered and the solid washed with EtOAc and dried giving pure N-(6-isobutyl-2-methyl-1H-inden-1-yl)acetamide (1.86 g, 31% yield) as a slightly brown-coloured solid. The filtrate was dried with MgSO$_4$, filtered, and the solvent evaporated. The crude product (3.26 g, brown solid) was triturated with hexane (20 ml), cooled to 5° C., filtered, washed with cold hexane (10 ml), and dried, giving additional N-(6-isobutyl-2-methyl-1H-inden-1-yl)acetamide (2.58 g, 100% pure, 43% yield; total yield: 74%) as a slightly brown-coloured solid.

R$_f$ (hexane/MTBE 11:1): 0.33; $^1$H-NMR (400 MHz, CDCl$_3$): δ 7.14 (br. s, 1H), 7.05 (br. d, J=7.5, 1H), 6.98 (br. d, J=7.5, 1H), 6.37 (br. s, 1H), 5.53 (br. d, J=9.3, 1H), 5.48 (br. d, J=9.4, 1H), 2.47 (d, J=7.1, CH$_2$), 2.08 (s, Me), 1.97 (br. s, COMe), 1.83 (hept., J=6.7, 1H), 0.89 (d, J=6.6, CMe$_2$); $^{13}$C-NMR (100 MHz, CDCl$_3$): δ 170.71 (s), 145.69 (s), 144.35 (s), 141.45 (s), 138.63 (s), 128.83 (d), 127.81 (d), 124.21 (d), 119.68 (d), 58.63 (d), 45.36 (t), 30.41 (d), 23.41 (q), 22.38 (2q), 14.09 (q); MS (EI): 244 (5), 243 (30), 201 (8), 200 (10), 186 (14), 185 (17), 184 (100), 158 (31), 144 (47), 143 (30), 142 (26), 141 (73), 128 (16), 115 (21), 43 (49).

Step 2:
N-(5-Isobutyl-2-methyl-1H-inden-3-yl)acetamide

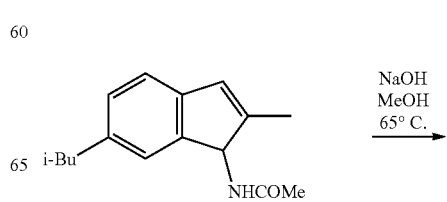

-continued

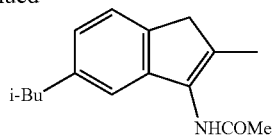

At 20° C., a suspension of N-(6-isobutyl-2-methyl-1H-inden-1-yl)acetamide (2 g, 8.22 mmol) in MeOH (20 ml) was treated dropwise with 2M aq. NaOH (2 ml, 4.0 mmol, 0.49 eq.) and the resulting suspension heated to reflux. The resulting solution was stirred at reflux for 1 h, cooled, treated with water (5 ml), and extracted with MTBE (20 ml). The organic phase was washed with aq. sat. NH$_4$Cl soln. (10 ml), with aq. sat. NaCl soln. (10 ml), dried over MgSO$_4$, filtered, and the solvent evaporated. The crude product (2 g, brown solid) was triturated with hexane (20 ml), cooled to 5° C., filtered, washed with cold hexane (10 ml), and dried, giving N-(5-isobutyl-2-methyl-1H-inden-3-yl)acetamide (1.73 g, 100% pure, 87% yield) as a slightly brown-coloured solid.

R$_f$ (hexane/MTBE 1:1): 0.12; $^1$H-NMR (400 MHz, CDCl$_3$): δ (main rotamer, 60%) 7.23 (br. d, J=8.0, 1H), 6.99 (br. d, J=8.0, 1H), 6.94-6.90 (m, 1H), 6.78-6.66 (br. s, 1H), 3.30 (br. s, CH$_2$), 2.49 (d, J=7.3, CH$_2$), 2.24 (s, Me), 2.03 (br. s, COMe), 1.86 (hept., J=6.7, 1H), 0.896 (d, J=6.6, CMe$_2$). δ (minor rotamer, 40%) 7.29 (br. d, J=7.3, 1H), 6.94-6.90 (m, 2H), 6.57-6.47 (br. s, 1H), 3.34 (br. s, CH$_2$), 2.51 (d, J=7.3, CH$_2$), 2.09 (br. s, COMe), 1.92 (s, Me), 1.86 (hept., J=6.7, 1H), 0.901 (d, J=6.6, CMe$_2$); $^{13}$C-NMR (100 MHz, CDCl$_3$): δ (main rotamer, 60%) 168.48 (s), 142.48 (s), 139.78 (s), 138.42 (s), 136.76 (s), 131.37 (s), 125.46 (d), 123.07 (d), 118.27 (d), 45.60 (t), 40.48 (t), 30.48 (d), 23.54 (q), 22.44 (2q), 14.19 (q). δ (minor rotamer, 40%) 173.34 (s), 142.80 (s), 140.44 (s), 139.86 (s), 136.03 (s), 133.13 (s), 126.03 (d), 123.41 (d), 118.43 (d), 45.48 (t), 40.23 (t), 30.48 (d), 22.37 (2q), 20.23 (q), 13.55 (q); MS (EI): 244 (6), 243 (36), 201 (8), 200 (16), 186 (21), 185 (15), 184 (100), 158 (38), 144 (60), 143 (41), 142 (24), 141 (49), 128 (16), 115 (17), 43 (59).

Step 3:
6-Isobutyl-2-methyl-2,3-dihydro-1H-inden-1-one

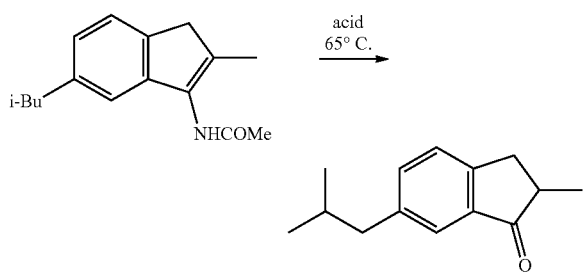

A suspension of N-(5-isobutyl-2-methyl-1H-inden-3-yl)acetamide (1.4 g, 5.75 mmol) in methanol (14 ml) and 35% aq. sulfuric acid (1.72 ml, 6.33 mmol, 1.1 eq.) was heated at reflux (65° C.) for 5 h, cooled, diluted with MTBE (20 ml), and washed with water (5 ml). The org. phase was washed with 2M aq. HCl and the combined aq. phases were extracted twice with MTBE (20 ml). The combined org. phases were washed with aqueous saturated NaHCO$_3$ (10 ml), with aqueous saturated NaCl (10 ml), dried with MgSO$_4$, filtered, and the solvent evaporated. The crude product (1.17 g, brown oil) was distilled using a Kugelrohr-distillation apparatus (0.09 mbar, 100-150° C.) giving 6-isobutyl-2-methyl-2,3-dihydro-1H-inden-1-one as characterized in Example 1 (1.03 g, 100% pure, 89% yield) as a slightly yellow oil.

Yield over 3 steps: 57%

Example 7: Preparation of 6-Bromo-2-methyl-2,3-dihydro-1H-inden-1-one—One-Pot Synthesis Using Methanesulfonamide (MeSO$_2$NH$_2$)

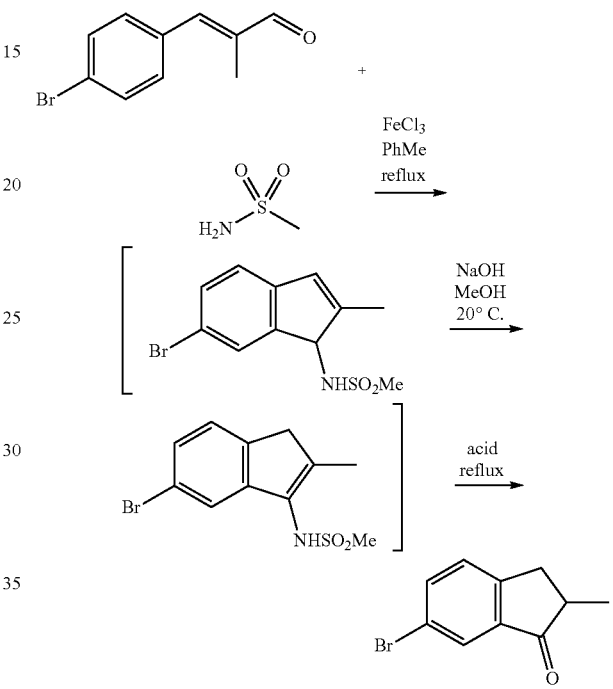

To a solution of (E)-3-(4-bromophenyl)-2-methylacrylaldehyde (50.0 g, 222 mmol, prepared from p-bromobenzaldehyde and propanal in the presence of NaOH in EtOH and water according to Unterhalt, B.; Ejabour, S. *Archiv Pharmazie* 1986, 319, 666-71) in toluene (200 ml) was added methanesulfonamide (25.4 g, 267 mmol, 1.2 eq.) and iron (III) chloride (7.21 g, 44.4 mmol, 0.2 eq.). The mixture was stirred and heated to 95° C. for 16 h. After the starting aldehyde was completely consumed, the reaction was cooled down, treated with methanol (200 ml) and a solution of sodium hydroxide (22.21 g, 555 mmol, 2.5 eq.) in water (70 ml), and stirred for 2 h at rt. The resulting mixture was then treated with methanol (200 ml) and dropwise with conc. HCl (54.7 ml, 37%, 666 mmol, 3.0 eq.), heated to 85° C., and stirred overnight. After cooling, water (200 ml) was added and the solution was extracted three times with MTBE (150 ml). The combined organic layers were washed with brine, dried with MgSO$_4$, filtered and concentrated. Flash-chromatography (silica gel, hexane/MTBE 50:1) of the residue gave a light yellow solid (23 g) that was distilled (bulb-to-bulb distillation apparatus, 150° C., 0.08 mbar) to give 6-bromo-2-methyl-2,3-dihydro-1H-inden-1-one (20 g, 96% purity, 38% yield) as a light yellow solid.

R$_f$ (hexane/MTBE 10:1): 0.3; $^1$H-NMR (300 MHz, CDCl$_3$): δ 7.86 (br. s, 1H), 7.67 (dd, J=8.1, 1.7, 1H), 7.34 (br. d, J=8.1, 1H), 3.35 (dd, J=17.2, 7.7, 1H), 2.83-2.62 (m, 2H), 1.31 (d, J=7.4, Me); $^{13}$C-NMR (75 MHz, CDCl$_3$): δ 207.7

(s), 151.9 (s), 138.1 (s), 137.3 (d), 128.2 (d), 126.8 (d), 121.5 (s), 42.4 (d), 34.6 (t), 16.1 (q); MS (EI): 226 (68), 224 (70), 211 (97), 209 (100), 198 (10), 196 (11), 183 (10), 181 (8), 170 (4), 156 (3), 145 (21), 128 (4), 115 (68), 102 (22), 89 (20), 75 (12), 63 (15).

Example 8: Preparation of 4-Bromo-2-methyl-2,3-dihydro-1H-inden-1-one—One-Pot Synthesis Using Methanesulfonamide (MeSO$_2$NH$_2$)

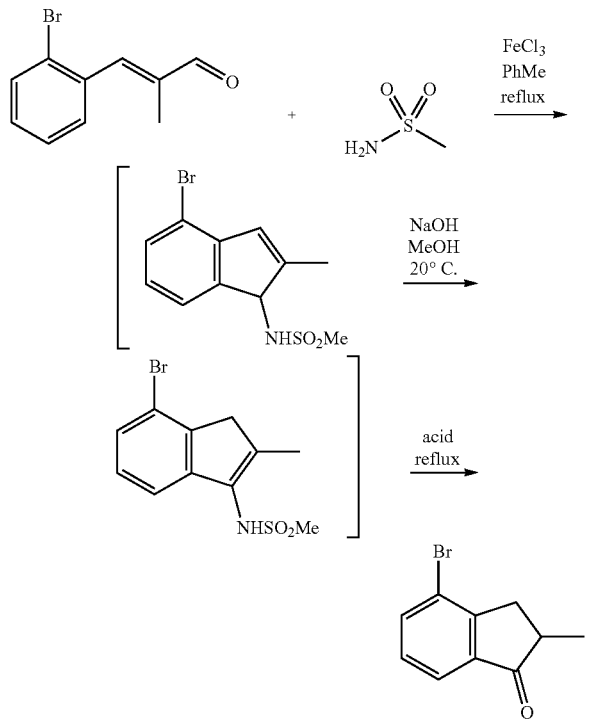

To a solution of (E)-3-(2-bromophenyl)-2-methylacrylaldehyde (70.0 g, 80% purity, 249 mmol, prepared from o-bromobenzaldehyde and propanal in the presence of NaOH in MeOH and water according to Li, W.-D. Z.; Duo, W.-G; Zhuang, C.-H. Org. Lett. 2011, 13, 3538-41) in toluene (200 ml) was added methanesulfonamide (28.4 g, 299 mmol, 1.2 eq.) and iron(III) chloride (8.07 g, 49.8 mmol, 0.2 eq.). The mixture was stirred and heated to 65° C. for 16 h. After the starting aldehyde was completely consumed, the reaction was cooled down, treated with methanol (200 ml) and a solution of sodium hydroxide (24.88 g, 622 mmol, 2.5 eq.) in water (80 ml), and stirred for 2 h at rt. The resulting mixture was then treated with methanol (200 ml) and dropwise with conc. HCl (63 ml, 37%, 746 mmol, 3.0 eq.), heated to 85° C., and stirred overnight. After cooling, water (200 ml) was added and the solution was extracted three times with MTBE (150 ml). The combined organic layers were washed with brine, dried with MgSO$_4$, filtered and concentrated. Flash-chromatography (silica gel, hexane/MTBE 50:1) of the residue gave a light yellow oil (34 g) that was distilled (bulb-to-bulb distillation apparatus, 130° C., 0.11 mbar) to give 4-bromo-2-methyl-2,3-dihydro-1H-inden-1-one (32 g, 61% yield) as a yellow solid.

R$_f$ (hexane/MTBE 10:1): 0.3; $^1$H-NMR (300 MHz, CDCl$_3$): δ 7.75 (d, J=7.7, 1H), 7.70 (d, J=7.6, 1H), 7.28 (t, J=7.6, 1H), 3.35 (dd, J=17.5, 7.7, 1H), 2.83-2.67 (m, 1H), 2.66 (dd, J=17.6, 3.8, 1H), 1.34 (d, J=7.4, Me); $^{13}$C-NMR (75 MHz, CDCl$_3$): δ 208.5 (s), 153.2 (s), 138.4 (s), 137.4 (d), 129.2 (d), 122.8 (d), 122.2 (s), 42.0 (d), 36.0 (t), 16.2 (q); MS (EI): 226 (51), 224 (53), 211 (97), 209 (100), 198 (10), 198(4), 196 (5), 183 (7), 181 (6), 170 (3), 168 (3), 156 (1), 145 (14), 128 (3), 127 (3), 115 (61), 102 (16), 89 (18), 75 (11), 63 (14).

Example 9: Preparation of 5- and 7-bromo-2-methyl-2,3-dihydro-1H-inden-1-one—One-Pot Synthesis Using Methanesulfonamide (MeSO$_2$NH$_2$)

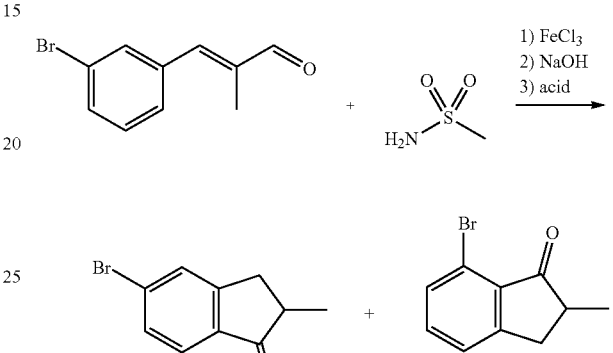

Similarly to examples 7 and 8, the sequential treatment of (E)-3-(3-bromophenyl)-2-methylacrylaldehyde (60.0 g, 267 mmol, prepared in 80% yield and 98% purity from m-bromobenzaldehyde and propanal in the presence of NaOH in MeOH and water) in toluene (200 ml) with first methanesulfonamide (30.4 g, 320 mmol, 1.2 eq.)/iron(III) chloride (8.65 g, 53.3 mmol, 0.2 eq.) at 65° C. for 16 h, then with methanol (200 ml)/sodium hydroxide (26.7 g, 666 mmol, 2.5 eq.) in water (70 ml) at rt. for 2 h, finally with methanol (200 ml)/conc. HCl (24.3 ml, 37%, 800 mmol, 3.0 eq.) at 85° C. overnight led after work-up and flash-chromatography (silica gel, hexane/MTBE 50:1) of the residue to a 85:15 mixture of 5- and 7-bromo-2-methyl-2,3-dihydro-1H-inden-1-one (33.3 g, 57% yield) as a yellow oil. Distillation (bulb-to-bulb distillation apparatus, 150° C., 0.08 mbar) gave a 85:15 mixture of 5- and 7-bromo-2-methyl-2,3-dihydro-1H-inden-1-one (30 g, 50% yield) as a yellow oil.

R$_f$ (hexane/MTBE 10:1): 0.3; $^1$H-NMR (300 MHz, CDCl$_3$): δ 7.65-7.35 (m, 3H), 3.46-3.28 (m, 1H), 2.83-2.67 (m, 1H), 2.79-2.62 (m, 2H), 1.32 (d, J=7.2, 0.45H, Me), 1.30 (d, J=7.2, 2.55H, Me); $^{13}$C-NMR (75 MHz, CDCl$_3$): δ (5-bromo-isomer) 208.0 (s), 155.0 (s), 135.2 (s), 131.0 (d), 130.0 (s), 129.8 (d), 125.2 (d), 42.0 (d), 34.6 (t), 16.2 (q); δ (7-bromo-isomer) 206.2 (s), 156.1 (s), 135.1 (d), 133.6 (s), 132.4 (d), 125.6 (d), 119.7 (s), 42.7 (d), 34.1 (t), 16.3 (q); MS (EI): 5-bromo-isomer: 226 (50), 224 (52), 211 (97), 209 (100), 198 (5), 196 (6), 183 (9), 181 (8), 170 (2), 168 (3), 156 (3), 154 (2), 145 (16), 128 (5), 127 (3), 115 (50), 102 (21), 89 (17), 75 (12), 63 (14); 7-bromo-isomer: 226 (57), 224 (59), 211 (97), 209 (100), 198 (10), 198(4), 196 (5), 183 (6), 181 (5), 170 (2), 168 (2), 156 (2), 145 (10), 128 (3), 115 (51), 102 (20), 89 (16), 75 (11), 63 (11).

Example 10: Preparation of 2-Ethyl-6-isobutyl-2,3-dihydro-1H-inden-1-one—One-Pot Synthesis Using Methanesulfonamide (MeSO₂NH₂)

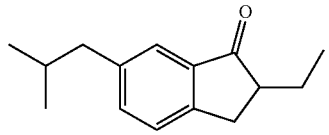 [SMILES: CCC1Cc2ccc(CC(C)C)cc2C1=O]

To a solution of (E)-3-(4-isobutylphenyl)-2-methylacrylaldehyde (5.35 g, 24.7 mmol) in toluene (50 ml) was added methanesulfonamide (2.82 g, 29.7 mmol) and iron(III) chloride (0.80 g, 4.9 mmol). The mixture was stirred and heated to 65° C. After the aldehyde was completely consumed (monitored by GC), the reaction was cooled to rt. Then methanol (30 ml) and a solution of sodium hydroxide (2.47 g, 61.8 mmol) in water (20 ml) was added, the mixture was stirred for 2 h at rt. Further methanol (30 ml) and sulfuric acid (3.95 mL, 74.2 mmol) was added, the mixture was heated to 70° C. and stirred overnight. Water (100 ml) was added and the solution was extracted with MTBE (100 ml×3). The combined organic layers were washed with brine, dried with MgSO₄, filtered and concentrated to give the crude product. The residue was purified by silica gel chromatography (hexane/MTBE=50:1) to give 4.0 g of product as light yellow oil. The oil was distilled via Kugelrohr (0.15 mbar, 160° C.) to give 2-ethyl-6-isobutyl-2,3-dihydro-1H-inden-1-one as colourless oil (2.60 g, 48.6% yield).

¹H NMR (300 MHz, CDCl₃): δ 7.52 (s, 1H), 7.34-7.40 (m, 2H), 3.28 (dd, J=17.1, 7.8 Hz, 1H), 2.78 (dd, J=17.1, 3.9 Hz, 1H), 2.58-2.65 (m, 1H), 2.52 (d, J=7.2 Hz, 2H), 1.80-2.04 (m, 1H), 1.46-1.60 (m, 1H), 1.01 (t, J=7.5 Hz, 3H), 0.90 (d, J=6.6 Hz, 6H) ppm; ¹³C NMR (75 MHz, CDCl₃): δ 209.2 (s), 151.5 (s), 141.1 (s), 137.0 (s), 136.0 (d), 126.1 (d), 123.8 (d), 49.2 (d), 44.9 (t), 32.0 (t), 30.2 (t), 24.5 (t), 22.3 (2q), 11.7 (q) ppm; GC/MS (EI): m/z (%): 216 (7) [M⁺], 188 (100), 173 (33), 145 (36), 131 (20), 91 (7), 77 (7).

Example 11: Preparation of 2-Isopropyl-6-methyl-2,3-dihydro-1H-inden-1-one—One-Pot Synthesis Using Methanesulfonamide (MeSO₂NH₂)

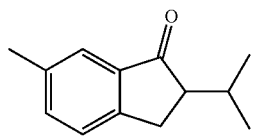

To a solution of (E)-3-methyl-2-(4-methylbenzylidene)butanal (3.00 g, 15.9 mmol) in toluene (100 ml) was added methanesulfonamide (2.27 g, 23.9 mmol) and iron(III) chloride (0.388 g, 2.39 mmol). The mixture was stirred and heated to 80° C. After the aldehyde was completely consumed (monitored by TLC), the reaction was cooled down and added methanol (30.0 ml) and sodium hydroxide (1.27 g, 31.9 mmol) in water (10.0 ml), the mixture was stirred for 2 h at rt. Further methanol (30 ml) and hydrogen chloride (3.78 ml, 39.8 mmol) was added, the mixture was heated to 70° C. and stirred overnight. Water (200 ml) was added and the solution was extracted with MTBE (150×3 ml). The combined organic layers were washed with brine, dried with MgSO₄, filtered and concentrated to give the crude product. The residue was purified by silica gel chromatography (hexane/MTBE=50:1) to give 0.8 g of product as light yellow oil. The oil was distilled via Kugelrohr (0.12 mbar, 140° C.) to give 0.500 g of product as colourless oil (26.7% yield).

¹H NMR (300 MHz, CDCl₃): δ 7.53 (s, 1H), 7.31-7.44 (m, 2H), 3.09 (dd, J=17.1, 9.0 Hz, 1H), 2.83-2.90 (m, 1H), 2.64-2.68 (m, 1H), 2.36-2.42 (m, 3H), 1.04 (d, J=6.9 Hz, 3H), 0.78 (d, J=6.6 Hz, 3H) ppm; ¹³C NMR (75 MHz, CDCl₃): δ 209.0 (s), 151.6 (s), 137.8 (s), 137.1 (s), 135.8 (d), 126.2 (d), 123.5 (d), 53.4 (d), 29.1 (d), 27.8 (t), 21.0 (q), 20.9 (q), 17.3 (q) ppm; GC/MS (EI): m/z (%): 188 (2) [M⁺], 173 (3), 146 (100), 131 (21), 115 (12), 91 (5), 77 (4).

Example 12: Preparation of 6-Ethyl-2-methyl-2,3-dihydro-1H-inden-1-one—One-Pot Synthesis Using Methanesulfonamide (MeSO₂NH₂)

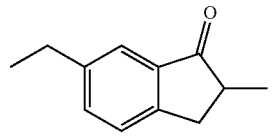

Prepared according to general procedure in Example 11, reaction of (E)-3-(4-ethylphenyl)-2-methylacrylaldehyde (5.0 g, 28.7 mmol), methanesulfonamide (4.09 g, 43.0 mmol) and iron(III) chloride (0.931 g, 5.74 mmol) followed by distillation through Kugelrohr (150° C./0.12 mbar) to give 6-ethyl-2-methyl-2,3-dihydro-1H-inden-1-one as a colorless oil (1.30 g, 26.0% yield).

¹H NMR (300 MHz, CDCl₃): δ 7.58 (s, 1H), 7.34-7.44 (m, 2H), 3.35 (dd, J=18.0, 8.7 Hz, 1H), 2.65-2.73 (m, 1H), 2.64-2.68 (m, 4H), 1.22-1.31 (m, 6H) ppm; ¹³C NMR (75 MHz, CDCl₃): δ 209.6 (s), 151.1 (s), 143.7 (s), 136.5 (s), 135.0 (d), 126.3 (d), 122.6 (d), 42.3 (d), 34.6 (t), 28.5 (t), 16.3 (q), 15.6 (q) ppm; GC/MS (EI): m/z (%): 174 (60) [M⁺], 159 (100), 145 (23), 131 (32), 115 (22), 91 (13), 77 (7).

Example 13: Preparation of 6-(sec-Butyl)-2-methyl-2,3-dihydro-1H-inden-1-one—One-Pot Synthesis Using Methanesulfonamide (MeSO₂NH₂)

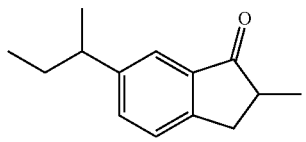

Prepared according to general procedure in Example 11, reaction of (E)-3-(4-(sec-butyl)phenyl)-2-methylacrylaldehyde (5.00 g, 14.8 mmol), methanesulfonamide (1.69 g, 17.8 mmol) and iron(III) chloride (0.481 g, 2.97 mmol) followed by distillation through Kugelrohr (150° C./0.08 mbar) to give 6-ethyl-2-methyl-2,3-dihydro-1H-inden-1-one as a colorless oil (1.00 g, 33.3% yield). (mixture of two isomers)¹H NMR (300 MHz, CDCl₃): δ 7.59 (s, 1H), 7.38-7.44 (m, 2H), 3.32-3.41 (m, 1H), 2.66-2.73 (m, 3H), 1.58-1.63 (m, 2H), 1.31 (d, J=7.2 Hz, 3H), 1.25 (d, J=6.9 Hz, 3H), 0.81 ppm (t, J=7.2 Hz, 3H) ppm; $^{13}$C NMR (75 MHz, CDCl$_3$): δ 209.8 (s), 151.3 (s), 147.2 (s), 136.5 (s), 134.4 (d), 134.3 (d), 126.3 (d), 121.9 (d), 121.9 (d), 42.4 (d), 41.4 (d), 34.6 (t), 31.1 (t), 21.9 (q), 16.3 (q), 12.2 (q) ppm; GC/MS (EI): m/z (%): 202 (30) [M$^+$], 187 (5), 173 (100), 159 (7), 117 (27), 91 (8), 77 (4).

Example 14: Preparation of 6-Isopentyl-2-methyl-2,3-dihydro-1H-inden-1-one—One-Pot Synthesis Using Methanesulfonamide (MeSO$_2$NH$_2$)

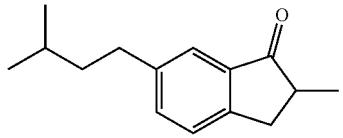 [SMILES: CC(C)CCc1ccc2c(c1)C(=O)C(C)C2]

Prepared according to general procedure in Example 11, reaction of (E)-3-(4-isopentylphenyl)-2-methylacrylaldehyde (5.00 g, 18.5 mmol), methanesulfonamide (2.11 g, 22.2 mmol) and iron(III) chloride (0.600 g, 3.70 mmol) followed by distillation through Kugelrohr (162° C./0.10 mbar) to give 6-isopentyl-2-methyl-2,3-dihydro-1H-inden-1-one as a colorless oil (1.30 g, 32.5% yield).

$^1$H NMR (300 MHz, CDCl$_3$): δ 7.57 (s, 1H), 7.32-7.42 (m, 2H), 3.34 (dd, J=18.0, 8.7 Hz, 1H), 2.62-2.70 (m, 4H), 1.46-1.62 (m, 3H), 1.29 (d, J=7.2 Hz, 3H), 0.93 (d, J=6.9 Hz, 6H) ppm; $^{13}$C NMR (75 MHz, CDCl$_3$): δ 209.5 (s), 151.0 (s), 142.5 (s), 136.5 (s), 135.4 (q), 126.3 (q), 123.1 (q), 42.3 (d), 40.8 (t), 34.6 (t), 33.3 (t), 27.5 (d), 22.5 (2q), 16.3 (q) ppm; GC/MS (EI): m/z (%): 216 (80) [M$^+$], 201 (30), 187 (1), 159 (98), 132 (100), 118 (55), 104 (55), 91 (23), 77 (8).

The invention claimed is:

1. A process of making a compound of formula (I)

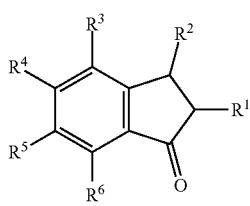

comprising the steps of:
a) addition of an amino compound H$_2$NR to a compound of formula (II)

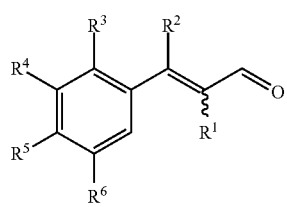

followed by cyclization to a compound of formula (III);

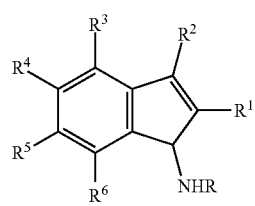

wherein the wavy bond in formula (II) indicates an unspecified configuration of the adjacent double bond; and the amino compound H$_2$NR is selected from the group consisting of alkylamides, sulfonamides and carbamates;

b) isomerization of compound of formula (III) to a compound of formula (IV);

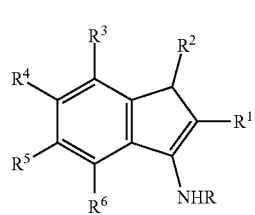

c) hydrolysis of compound of formula (IV) to compound of formula (I);

wherein, in the compounds of formula (I), (II), (III) and/or (IV),

R$^1$ represents methyl, ethyl, ethenyl, a linear, branched or cyclic C3-10 alkyl or alkenyl group, or a phenyl group, optionally substituted; and R$^2$, R$^3$, R$^4$, R$^5$ and R$^6$ each independently represent a hydrogen atom, methyl, ethyl, ethenyl, methoxy, ethoxy, ethenoxy, a linear, branched or cyclic C3-10 alkyl, alkenyl or alkoxy group, a halogen atom or a phenyl group, optionally substituted, and wherein the process is carried out in a one-pot procedure.

2. The process according to claim 1, wherein the amino compound H$_2$NR is an alkylamide, and R represents —(CO)Me or —(CO)Et.

3. The process according to claim 1, wherein the amino compound H$_2$NR is a sulfonamide, and R represents —SO$_2$Me, —SO$_2$Et or —SO$_2$PhMe.

4. The process according to claim 1, wherein the amino compound H$_2$NR is a carbamate, and R represents —CO$_2$Me, —CO$_2$Et.

* * * * *